United States Patent
Hooper

(10) Patent No.: US 10,443,106 B2
(45) Date of Patent: Oct. 15, 2019

(54) METHODS AND COMPOSITIONS FOR IDENTIFYING SULFUR AND IRON MODIFYING BACTERIA

(71) Applicant: AdvaTect Diagnostics, LLC, Carollton, TX (US)

(72) Inventor: Dennis G. Hooper, Lewisville, TX (US)

(73) Assignee: Advatect Diagnostics, LLC, Carrollton, TX (US)

( * ) Notice: Subject to any disclaimer, the term of this patent is extended or adjusted under 35 U.S.C. 154(b) by 504 days.

(21) Appl. No.: 14/590,173

(22) Filed: Jan. 6, 2015

(65) Prior Publication Data

US 2015/0125861 A1  May 7, 2015

Related U.S. Application Data

(63) Continuation of application No. 12/901,247, filed on Oct. 8, 2010, now Pat. No. 8,962,251.

(60) Provisional application No. 61/249,857, filed on Oct. 8, 2009.

(51) Int. Cl.
  *C12Q 1/68* (2018.01)
  *C12Q 1/6895* (2018.01)
  *C12Q 1/689* (2018.01)

(52) U.S. Cl.
  CPC .......... *C12Q 1/6895* (2013.01); *C12Q 1/689* (2013.01); *C12Q 2600/112* (2013.01); *C12Q 2600/156* (2013.01)

(58) Field of Classification Search
  None
  See application file for complete search history.

(56) References Cited

U.S. PATENT DOCUMENTS

| | | | |
|---|---|---|---|
| 4,683,202 A | 7/1987 | Muller et al. | |
| 4,744,981 A | 5/1988 | Pavansasivam | |
| 4,772,551 A | 9/1988 | Hart et al. | |
| 4,800,159 A | 1/1989 | Muller et al. | |
| 4,835,100 A | 5/1989 | Dixon | |
| 4,906,452 A | 3/1990 | Sivam | |
| 5,261,394 A | 11/1993 | Mulligan et al. | |
| 5,426,027 A | 6/1995 | Lott et al. | |
| 5,707,802 A | 1/1998 | Sandhu | |
| 5,776,694 A | 7/1998 | Sheiness et al. | |
| 5,922,855 A | 7/1999 | Liskay | |
| 6,210,345 B1 | 4/2001 | Van Brunt | |
| 6,268,222 B1 | 7/2001 | Chandler et al. | |
| 6,345,025 B1 | 2/2002 | Yamamiya | |
| 6,362,008 B1 | 3/2002 | Kohn et al. | |
| 6,372,430 B1 | 4/2002 | Morrison et al. | |
| 6,696,304 B2 | 2/2004 | Davies | |
| 6,699,670 B2 | 3/2004 | Rothman et al. | |
| 6,846,631 B2 | 1/2005 | Beck et al. | |
| 6,872,523 B1 | 3/2005 | Iwen et al. | |
| 7,384,622 B2 | 6/2008 | Hata et al. | |
| 7,601,530 B2* | 10/2009 | Sugio | C12N 1/20 424/93.1 |
| 8,628,928 B2 | 1/2014 | Hooper | |
| 8,956,821 B2 | 2/2015 | Hooper | |
| 8,962,251 B2 | 2/2015 | Hooper | |
| 9,103,829 B2 | 8/2015 | Hooper | |
| 9,150,934 B2 | 10/2015 | Hooper | |
| 9,182,398 B2 | 11/2015 | Hooper | |
| 9,487,836 B2 | 11/2016 | Hooper | |
| 2001/0004813 A1 | 6/2001 | Hedman | |
| 2002/0028487 A1 | 3/2002 | La Thangue | |
| 2002/0061545 A1 | 5/2002 | Choi | |
| 2003/0050470 A1 | 3/2003 | An | |
| 2003/0054356 A1 | 3/2003 | Jacobson et al. | |
| 2003/0129600 A1 | 7/2003 | Morrison et al. | |
| 2003/0203412 A1 | 10/2003 | Vojdani | |
| 2004/0023207 A1 | 2/2004 | Polansky | |
| 2004/0166492 A1 | 8/2004 | Engel et al. | |
| 2004/0170981 A1 | 9/2004 | McKenney et al. | |
| 2004/0209241 A1 | 10/2004 | Hermanson | |
| 2005/0176023 A1 | 8/2005 | Ramon et al. | |
| 2005/0233314 A1 | 10/2005 | Juang et al. | |
| 2007/0026452 A1 | 2/2007 | Matalon | |

(Continued)

FOREIGN PATENT DOCUMENTS

| | | |
|---|---|---|
| EP | 1215282 | 6/2002 |
| JP | 2008005760 | 1/2008 |

(Continued)

OTHER PUBLICATIONS

Jang et al. (Environmental Engineering Science 2003, 20(3): 183-196).*
Wulf-Durand et al. (Appl Environ Microbiol, 1997, 63(7):2944).*
Lowe et al. (Nucleic Acids Research, 1990, 18(7):1757-1761).*
Pizarro et al. (Appl. Environ. Microbiol. 62 (4), 1323-1328 (1996)).*
X91225 Accession No. 2003 (Year: 2003).*
Pestka et al. (Toxicological Sciences, 2008, 104(1):4-26) (Year: 2008).*
Koster et al, "A geographically diverse set of isolates indicates two phylogenetic lineages within Strachybotrys Chartarum," Can. J. Bot., 2003; 81: 633-643.
Niesters et al, "Rapid, polymerase chain reaction-based identification assays for *Candida* species," Journal of Clinical Microbiology, 1993, 904-910.

(Continued)

*Primary Examiner* — Stephanie K Mummert
(74) *Attorney, Agent, or Firm* — Barnes & Thornburg, LLP

(57) ABSTRACT

The invention relates to methods and compositions for identifying specific bacterial species, which are sulfur and iron oxidizers and/or reducers, from wall board (e.g., dry wall) and/or a patient tissue or body fluid. The method comprises the steps of extracting and recovering DNA of the bacterial species from the wall board and/or the patient tissue or body fluid, amplifying the DNA, hybridizing a probe to the DNA to specifically identify the bacterial species, and specifically identifying the bacterial species. Kits and nucleic acids for use in the methods are also provided. Methods for eliminating the sulfur and iron oxidizing and/or reducing bacteria from wall board using a zeolite are also provided.

11 Claims, No Drawings

Specification includes a Sequence Listing.

(56) References Cited

U.S. PATENT DOCUMENTS

| | | |
|---|---|---|
| 2007/0202584 A1* | 8/2007 | Ohtsuka et al. ......... C12P 3/00 435/168 |
| 2008/0014582 A1 | 1/2008 | Hooper |
| 2008/0108905 A1 | 5/2008 | Lurie |
| 2010/0068718 A1 | 3/2010 | Hooper |
| 2010/0075322 A1 | 3/2010 | Hooper |
| 2010/0129821 A1 | 5/2010 | Fredricks |
| 2011/0104684 A1 | 5/2011 | Hooper |
| 2012/0214897 A1 | 8/2012 | Yiannikouris |
| 2013/0059307 A1 | 3/2013 | Hooper |
| 2013/0183697 A1 | 7/2013 | Hooper |
| 2014/0221504 A1 | 8/2014 | Hooper |
| 2014/0342927 A1 | 11/2014 | Hooper |
| 2015/0125860 A1 | 5/2015 | Hooper |
| 2015/0125861 A1 | 5/2015 | Hooper |
| 2015/0176087 A1 | 6/2015 | Hooper |
| 2015/0337396 A1 | 11/2015 | Hooper |
| 2016/0313329 A1 | 11/2016 | Hooper |
| 2017/0137896 A1 | 5/2017 | Hooper |
| 2017/0336410 A1 | 11/2017 | Hooper |

FOREIGN PATENT DOCUMENTS

| | | |
|---|---|---|
| WO | WO96/21741 | 7/1996 |
| WO | WO98/50584 | 11/1998 |
| WO | WO01/54653 | 8/2001 |
| WO | WO04/054359 | 7/2004 |
| WO | WO07/023461 | 3/2007 |
| WO | WO 2008/051285 | 5/2008 |
| WO | 20100121578 | 10/2010 |
| WO | 20140197607 | 12/2014 |
| WO | 2017049120 | 3/2017 |

OTHER PUBLICATIONS

Chen et al, "Identification of medically important yeases using PCR-based detection of DNA sequence polymorphisms in the internal transcribed spacer 2 region of the rRNA genes," Journal of Clinical Microbiology, 2000; 2302-2310.
Henry et al., "Identification of *Apsergillus* species using internal transcribed spacer regions 1 and 2," Journal of Clinical Microbiology, 2000; 1510-1515.
Fontelo, "Detection of T-2 toxin by an improved radioimmunoassay," Applied and Environmental Microbiology, 1983; 45(2):640-643.
Brasel et al, "Detection of airborne Stachybotrys chartarum macrocyclic trichothecene mycotoxins on particulates smaller than conidia," Applied and Environmental Microbiology, 2005; 71:114-122.
Kierek-Jaszcuk et al., "Detection and quantification of the T-2 mycotoxin by ELISA utilizing toxin-specific polyclonal antibodies raised in chickens," Food and Agricultural Immunology, 1995; 7:243-252.
Groopman et al, "High-affinity monoclonal antibodies for aflatoxins and their application to solid-phase immunoassays," P.N.A.S., 1984; 81:7728-7731.
Vetro, Thesis: Development of sensitive immunodiagnostics for determination of toxic residues (mycotoxins, drugs) in biological fluids and animal feeds, 2002.
Lewis et al., "Detection of gliotoxin in experimental and human aspergillosis," *Infection and Immunity*; 2005; 73(1): 635-637.
Spiess et al., "Development of a LightCycler PCR assay for detection and qualification of *Aspergillus fumigatus* DNA in clinical samples from neutropenic patients," *Journal of Clinical Microbiology*, 2003; 41(5): 1811-1818.
Fox et al., "Detection of *Aspergillus fumigatus* mycotoxins: immunogen synthesis and immunoassay development," *Journal of Microbiological Methods*, 2004; 6+: 221-230.
Bialek et al., "PCR based identification and discrimination of agents of mucomycosis and aspergillosis in paraffin wax embedded tissue," *J. Clin. Pathol.*, 2005; 58:1180-1184.

Zorgani et al,., "Detection pyrogenic toxin of *Staphylococcus aureus* in sudden infant death syndrome," *FEMS Immunology and Medical Microbiology*, 1999; 25: 103-108.
Stack et al., "Nonribosomal peptide synthesis in *Apergillus fumigates* and other fungi," *Microbiology*, 2007; 153(5): 1297-1306.
Ferns, "Evaluation of the role of real-time PCR in the diagnosis of invasive aspergillosis," *Leukemia & Lymphoma*, 2006; 41(1): 15-20.
Cruz-Perez et al., Detection and quantitation of *Aspergillus fumigatus* in pure culture using polymerase chain reaction, *Molecular and Cellular Probes*, 2001; 15:81-88.
GenBank AF138288 [online] Apr. 11, 2000 [retrieved on Feb. 23, 2012] retrieved from http://www.ncbi.nlm.nih.gov/nuccore/af138288.
De Vries et al. "*Aspergillus vadensis*, a new species of the group of black Aspergilli," Antoine Van Leeuwenhoek, 2005; 87(3): 195-203.
Ahern, *The Scientist*, 1995; 20(15):1-9.
Nielsen et al., "Yeast populations associated with Ghanaian cocoa fermentations analyzed using denaturing gradient gel electrophoresis (DGGE)," *Yeast*; 2005; 22:271-284.
Bennett et al., "Mycotoxins," *Clin. Microbiol. Rev.*, 2003; 16(3):497-516.
Lee et al., J. Assoc. Off. Anal. Chem., 1989, 72(2): 345-348.
Brasel at el., Archives of Environmental Health: An international Journal, Jun. 2004, 59(6): 317-323.
Zinkevich et al., FEMS Microbiology Ecology, 2000, 34: 147-155.
Andersson et al., Appl Environ Microbiol, 1997, 63(2): 387-393.
Quatrini et al., Hydrometallurgy, 2006, 83: 263-272.
U.S. Appl. No. 14/590,151, unpublished.
Wulf-Durand et al., Appl. Environ. Microbiol., 1997, 63(7): 2944-2948.
Gregory et al., Toxicology Pathol., 2004, 32: 26-34.
Lee et al., J. Agric. Food Chem., 1990, 38: 444-448.
QuantiTox Kit from EviroLogix (Jul. 12, 2004).
Llobet-Brossa et al., Aquatic Microbial Ecol, 2002, 29: 211-226.
Yamanaka, Biochemistry and Environmental Biology: Chemolithoautotrophic Bacteria, 2008, pp. 7-9.
Bata et al., Appl Environ Microbiol, Mar. 1985, 49(3): 678-681.
McCormick et al., Toxins, 2011, 3: 802-814.
Willinger et al., Journal of Clinical Microbiology, 2003, 41(2): 581-585.
De Aguirre et al., Journal of Clinical Microbiology, 2004, 42(8): 3495-3504.
Hinrikson et al., Journal of Clinical Microbiology, 2005, 43(5): 2092-2103.
GenBank AF 138287 [online] Apr. 11, 2000 [retrieved Sep. 20, 2014] retrieved from http://www.ncbi.nlm.nih.gov/nuccore/af138287.
Wei et al., Anal Biochem., Feb. 1987, 160(2): 399-408.
Brasilerio et al., "Genetic variability within *Fusarium solani* specie as revealed by PCR-fingerprinting based on pcr markers," Brazilian Journal of Microbiology, 2004, 35: 205-210.
Suga et al., "Phylogenetic analysis of the phytopathogenic fungus *Fusarium solani* cased on the rDNA-ITS region," Mycological Research, 2000, 104(10): 1175-1183.
Haugland et al., "Identification of putative sequence specific PCR primers for detection of the toxigenic fungal species *Stachybotrys chartarum*," Mol Cell Probes, Dec. 1998, 12(6): 387-96.
Mackay et al., "Real-time PCR in the microbiology laboratory," Clin. Microbiol. Infect., 2004, 10: 190-212.
International Search Report/Written Opinion for PCT/US07/08249, dated Oct. 17, 2008.
Landlinger et al., Species-specific identification of a wide range of clinically relevant fungal pathogens by use of Luninex xmap technology, Journal of Clinical Microbiology, 2009, 47(4): 1063-1073.
Shin et al.. J. Clin. Micro., 1999, 37(1): 165-170.
Lowe et al., Nucleic Acid Research, 1990, 18(7): 1757-1761.
Lengerova et al., Journal of Clinical Microbiology, 2012, 50(3): 602-608.
GenBank KP412260.1 [online] Feb. 1, 2015 [retrieved on Oct. 9, 2015] retrieved from: https://www.ncbi.nlm.nih.gov/nuccore/kp412260.

(56) References Cited

OTHER PUBLICATIONS

Lo, Methods in Microbiology 336, Humana Press (2006) front matter and pp. 1-10 (21 total pages).
Santa Lucia, J. Methods in Molecular Biology 402, Humana Press (2007) front matter and pp. 3-33 (40 total pages).
Eurogentec [online] May 24, 2005 [ retrieved on Nov. 3, 2013] retrieved from http://web.archive.org/web/20050524042658/http://www.gene-quantification.de/eurogentec-RT-PCR-booklet.pdf.

* cited by examiner

METHODS AND COMPOSITIONS FOR IDENTIFYING SULFUR AND IRON MODIFYING BACTERIA

CROSS REFERENCE TO RELATED APPLICATIONS

This application is a continuation of U.S. application Ser. No. 12/901,247, filed Oct. 8, 2010, which claims priority under 35 U.S.C § 119(e) to U.S. Provisional Application Ser. No. 61/249,857, filed on Oct. 8, 2009, and incorporated by reference herein in their entirety.

FIELD OF THE INVENTION

This invention relates to methods and compositions for detecting or identifying sulfur and iron reducing and/or oxidizing bacteria. More particularly, the invention relates to methods and compositions for identifying sulfur and iron reducing and/or oxidizing bacteria in 1) wall board and/or 2) patient tissues or body fluids.

BACKGROUND AND SUMMARY

Iron and sulfur reducing and/or oxidizing bacteria are important for use in the leaching of certain ores to extract heavy metals. The ability of these organisms to leach ores is due to the possession of unique enzyme systems that can oxidize and/or reduce both iron ($Fe^{+2}$) and sulfur compounds. For example, acidophilic thiobacilli are major bacteria in the leaching of sulfide ores at low pH. These bacteria are able to derive energy and reducing power for growth from the oxidation of ferrous iron and inorganic sulfur compounds, such as elemental sulfur, sulfide, thiosulfate, and polythionate. Studies have also demonstrated that these organisms possess enzymes to reduce metals and inorganic sulfur compounds as well. Generally, these organisms can be acidophilic, autotrophic, and chemolithotrophic.

For example, *Thiobacillus ferroxidans* has two kinds of sulfur reducing enzyme systems, namely a pH 1.5 sulfur-reducing system and a pH 7.5 sulfur-reducing system which produce $H_2S$ from elemental sulfur. It has also been demonstrated that $H_2S$ is produced from tetrathionate via a two-step reaction by *Thiobacillus ferrooxidans*. This two-step reaction comprises: 1) decomposition of tetrathionate by a tetrathionate-decomposing enzyme to provide elemental sulfur and trithionate, and 2) reduction of the elemental sulfur produced to $H_2S$.

Zeolites are microsporous, aluminosilicate minerals used as commercial adsorbents. The term zeolite was originally coined in 1756 by Swedish mineralogist who observed that upon rapidly heating the material stilbite, it produced large amounts of steam from water that had been adsorbed by the material. Zeolites have a porous structure that can accommodate a wide variety of cations, such as $Na^+$, $K^+$, $Ca^{2+}$, $Mg^{2+}$ and others. These positive ions are rather loosely held and can readily be exchanged for others in a contact solution.

Recently, some imported dry wall from Chinese wall board manufacturers has been found to emit numerous noxious and toxic gases, such as hydrogen sulfide and approximately 10 other noxious gases, once the wall board has been exposed to atmospheric conditions of increased humidity and increased dew point. The wall board (e.g., dry wall) becomes moist and emits gases which cause respiratory problems, sinusitis, skin irritation, and vision problems. For example, these emitted gases can cause a disproportionate number of illnesses for the inhabitants of homes with the wall board. An explanation why the wall board (e.g., dry wall) exudes such gases is needed to be able to prevent these illnesses from occurring and to be able to treat patients with these illnesses.

Applicant has discovered iron and sulfur reducing and/or oxidizing bacteria in wall board, and these organisms are likely the cause of the gases exuded from the wall board with the resulting illnesses for the inhabitants of homes with the wall board. The bacterial contaminants that can inundate the indoor environment from these bacteria include substances such as microbial volatile organic compounds (MVOC), allergenic proteins, inorganic compounds and gases, and organic compounds and gases.

Bacteria have typically been identified based on growth characteristics on specific selective media, and by either biochemical or carbohydrate utilization of specific compounds. These identification methods are based on the knowledge that a specific genus or species of bacteria produce or do not produce enzymes that utilize specific chemicals or carbohydrates for growth. Because these methods may require specific media and growth on these media for days to weeks for an identification to be made, these methods are time consuming. These methods are also inaccurate because not all of the organisms in a sample will be culturable, inevitably leading to the possible misidentification of the organism.

Thus, the invention further provides methods and compositions for the specific, sensitive, and rapid detection and identification of iron and sulfur reducing and/or oxidizing bacteria in wall board, such as dry wall. Applicant has developed bacterial DNA extraction procedures from wall board, such as dry wall, and has supplemented those methods by developing detection and identification methods. The detection and identification methods employ amplification of DNA probes and primers that specifically and selectively amplify bacterial DNA isolated from samples of wall board, such as dry wall. Kits and compositions for detecting and identifying iron and sulfur reducing and/or oxidizing bacteria in wall board, such as dry wall, are also provided. For example, acidophilic thiobacilli can be detected. Furthermore, iron and sulfur reducing and oxidizing bacteria such as *Acidothiobacillus* (*thiobacillus*) *ferrooxidans, Thiobacillus thiooxidans, Leptospirillium ferroxidans, Thiobacillus caldus, Sulfobacillus thermosulfidooxidans*, and *Desulfotomaculum ruminis* can be detected.

The invention also provides methods and compositions for the specific, sensitive, and rapid detection and identification of iron and sulfur reducing and/or oxidizing bacteria in patient tissues and body fluids. The detection and identification methods employ amplification of DNA probes and primers that specifically and selectively amplify bacterial DNA isolated from patient tissues and body fluids. Kits and compositions for detecting and identifying iron and sulfur reducing and/or oxidizing bacteria in patient tissues and body fluids are also provided. For example, acidophilic thiobacilli can be detected and identified. Furthermore, iron and sulfur reducing and/or oxidizing bacteria such as *Acidothiobacillus* (*thiobacillus*) *ferrooxidans, Thiobacillus thiooxidans, Leptospirillium ferroxidans, Thiobacillus caldus, Sulfobacillus thermosulfidooxidans*, and *Desulfotomaculum ruminis* can be detected and identified.

The invention also provides a method of treating wall board with a zeolite to eliminate a sulfur and iron reducing and/or oxidizing bacterial species in the wall board. Illustratively, the zeolite can comprise elemental ions (e.g., $Ca^{+2}$, $Mg^{+2}$, etc.) that bind to the sulfur and iron reducing and/or oxidizing bacterial species and limit the growth of these organisms.

In one embodiment, multiple iron and sulfur reducing and/or oxidizing bacterial species can be identified in either wall board or patient tissues or body fluids using a PCR-based reaction, saving money and time while insuring that the methodology is highly specific and accurate.

In one illustrative embodiment, a method is provided of identifying a specific iron and sulfur reducing and/or oxidizing bacterial species in wall board. The method comprises the steps of extracting and recovering DNA of the bacterial species from the wall board, amplifying the DNA, hybridizing a probe to the DNA to specifically identify the bacterial species, and specifically identifying the bacterial species.

In still another embodiment, a method is provided of determining if a patient is at risk for or has developed a disease state related to an infection with a specific iron and sulfur reducing and/or oxidizing bacterial species. The method comprises the steps of extracting and recovering DNA of the specific bacterial species from a tissue or body fluid of the patient, amplifying the DNA, hybridizing a probe to the DNA to specifically identify the bacterial species, and specifically identifying the bacterial species.

In another illustrative embodiment, a method is provided of identifying a specific iron and sulfur reducing and/or oxidizing bacterial species in a patient tissue or a body fluid. The method comprises the steps of extracting and recovering DNA of the specific bacterial species from a tissue or body fluid of the patient, amplifying the DNA, hybridizing a probe to the DNA to specifically identify the bacterial species, and specifically identifying the bacterial species.

In yet another embodiment, a kit is provided. The kit comprises components for the extraction and recovery of the DNA of a sulfur and iron reducing and/or oxidizing bacterial species from wall board. The kit can further comprise instructions for the extraction and recovery of the sulfur and iron reducing and/or oxidizing bacterial species from the wall board.

In still another illustrative embodiment, a kit is provided. The kit comprises components for identification of a sulfur and iron reducing and/or oxidizing bacterial species. The kit components for identification of the sulfur and iron reducing and/or oxidizing bacterial species can be selected from the group consisting of a purified nucleic acid comprising a sequence of SEQ ID NO: 1 to SEQ ID NO: 18, a heat stable DNA polymerase, a buffer, $MgCl_2$, $H_2O$, and instructions for use.

In another embodiment, a kit is provided. The kit comprises components for the extraction and recovery of a sulfur and iron reducing and/or oxidizing bacterial species from wall board and components for identification of the sulfur and iron reducing and/or oxidizing bacterial species. The kit can further comprise any of the components described in the preceding paragraphs.

In another embodiment, a purified nucleic acid is provided. The purified nucleic acid comprises a sequence of SEQ ID NO: 1 to SEQ ID NO: 18 or a sequence that hybridizes under highly stringent conditions to a sequence consisting of SEQ ID NO: 1 to SEQ ID NO: 18.

In still another embodiment, a purified nucleic acid is provided. The purified nucleic acid comprises a complement of a sequence of SEQ ID NO: 1 to SEQ ID NO: 18 or a sequence that hybridizes under highly stringent conditions to a complement of a sequence consisting of SEQ ID NO: 1 to SEQ ID NO: 18.

In yet another illustrative embodiment, a method of treating wall board to eliminate a sulfur and iron reducing and/or oxidizing bacterial species in the wall board is provided. The method comprises the steps of treating the wall board with a zeolite, and eliminating the sulfur and iron reducing and/or oxidizing bacterial species in the wall board.

The following embodiments are also contemplated:

1. A method of identifying a specific iron and sulfur reducing and/or oxidizing bacterial species in wall board, the method comprising the steps of:

extracting and recovering DNA of the bacterial species from the wall board, amplifying the DNA;

hybridizing a probe to the DNA to specifically identify the bacterial species; and specifically identifying the bacterial species.

2. The method of clause 1 wherein the amplifying step is performed with a primer that hybridizes to the DNA.

3. The method of any one of clauses 1 or 2 wherein the wall board is dry wall.

4. The method of any one of clauses 1 to 3 wherein the DNA is amplified using PCR.

5. The method of clause 4 wherein the PCR is real-time PCR.

6. The method of any one of clauses 1 to 5 wherein the probe is fluorescently labeled.

7. The method of any one of clauses 2 to 6 wherein the primer is fluorescently labeled.

8. The method of any one of clauses 1 to 7 wherein the bacterial species is selected from the group consisting of *Acidothiobacillus ferrooxidans*, *Thiobacillus thiooxidans*, *Leptospirillium ferroxidans*, *Thiobacillus caldus*, and *Desulfotomaculum ruminis*.

9. The method of any one of clauses 1 to 8 wherein the probe, a forward primer, and a reverse primer are used during the amplification step and the probe comprises the sequence of SEQ ID NO: 1, the forward primer comprises the sequence of SEQ ID NO: 2, and the reverse primer comprises the sequence of SEQ ID NO: 3.

10. The method of any one of clauses 1 to 8 wherein the probe, a forward primer, and a reverse primer are used during the amplification step and the probe comprises the sequence of SEQ ID NO: 4, the forward primer comprises the sequence of SEQ ID NO: 5, and the reverse primer comprises the sequence of SEQ ID NO: 6.

11. The method of any one of clauses 1 to 8 wherein the probe, a forward primer, and a reverse primer are used during the amplification step and the probe comprises the sequence of SEQ ID NO: 7, the forward primer comprises the sequence of SEQ ID NO: 8, and the reverse primer comprises the sequence of SEQ ID NO: 9.

12. The method of any one of clauses 1 to 8 wherein the probe, a forward primer, and a reverse primer are used during the amplification step and the probe comprises the sequence of SEQ ID NO: 10, the forward primer comprises the sequence of SEQ ID NO: 11, and the reverse primer comprises the sequence of SEQ ID NO: 12.

13. The method of any one of clauses 1 to 8 wherein the probe, a forward primer, and a reverse primer are used during the amplification step and the probe comprises the sequence of SEQ ID NO: 13, the forward primer comprises the sequence of SEQ ID NO: 14, and the reverse primer comprises the sequence of SEQ ID NO: 15.

14. The method of any one of clauses 1 to 8 wherein the probe, a forward primer, and a reverse primer are used during the amplification step and the probe comprises the sequence of SEQ ID NO: 16, the forward primer comprises the sequence of SEQ ID NO: 17, and the reverse primer comprises the sequence of SEQ ID NO: 18.

15. A method of identifying a specific iron and sulfur reducing and/or oxidizing bacterial species in a patient tissue or a body fluid, the method comprising the steps of:
  extracting and recovering DNA of the bacterial species from the patient tissue or body fluid;
  amplifying the DNA;
  hybridizing a probe to the DNA to specifically identify the bacterial species; and
  specifically identifying the bacterial species.

16. The method of clause 15 wherein the amplifying step is performed with a primer that hybridizes to the DNA.

17. The method of any one of clauses 15 or 16 wherein the patient tissue and the body fluid are selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma.

18. The method of any one of clauses 15 to 17 wherein the DNA is amplified using PCR.

19. The method of clause 18 wherein the PCR is real-time PCR.

20. The method of any one of clauses 15 to 19 wherein the probe is fluorescently labeled.

21. The method of any one of clauses 16 to 20 wherein the primer is fluorescently labeled.

22. The method of any one of clauses 15 to 21 wherein the bacterial species is selected from the group consisting of *Acidothiobacillus ferrooxidans, Thiobacillus thiooxidans, Leptospirillium ferroxidans, Thiobacillus caldus*, and *Desulfotomaculum ruminis*.

23. The method of any one of clauses 15 to 22 wherein the probe, a forward primer, and a reverse primer are used during the amplification step and the probe comprises the sequence of SEQ ID NO: 1, the forward primer comprises the sequence of SEQ ID NO: 2, and the reverse primer comprises the sequence of SEQ ID NO: 3.

24. The method of any one of clauses 15 to 22 wherein the probe, a forward primer, and a reverse primer are used during the amplification step and the probe comprises the sequence of SEQ ID NO: 4, the forward primer comprises the sequence of SEQ ID NO: 5, and the reverse primer comprises the sequence of SEQ ID NO: 6.

25. The method of any one of clauses 15 to 22 wherein the probe, a forward primer, and a reverse primer are used during the amplification step and the probe comprises the sequence of SEQ ID NO: 7, the forward primer comprises the sequence of SEQ ID NO: 8, and the reverse primer comprises the sequence of SEQ ID NO: 9.

26. The method of any one of clauses 15 to 22 wherein the probe, a forward primer, and a reverse primer are used during the amplification step and the probe comprises the sequence of SEQ ID NO: 10, the forward primer comprises the sequence of SEQ ID NO: 11, and the reverse primer comprises the sequence of SEQ ID NO: 12.

27. The method of any one of clauses 15 to 22 wherein the probe, a forward primer, and a reverse primer are used during the amplification step and the probe comprises the sequence of SEQ ID NO: 13, the forward primer comprises the sequence of SEQ ID NO: 14, and the reverse primer comprises the sequence of SEQ ID NO: 15.

28. The method of any one of clauses 15 to 22 wherein the probe, a forward primer, and a reverse primer are used during the amplification step and the probe comprises the sequence of SEQ ID NO: 16, the forward primer comprises the sequence of SEQ ID NO: 17, and the reverse primer comprises the sequence of SEQ ID NO: 18.

29. A kit comprising a purified nucleic acid with a sequence selected from the group consisting of SEQ ID NO: 1 to SEQ ID NO: 18 or with a complement of a sequence selected from the group consisting of SEQ ID NO: 1 to SEQ ID NO: 18.

30. A kit comprising components for the extraction and recovery of a sulfur and iron reducing and/or oxidizing bacterial species from wall board.

31. The kit of clause 30 further comprising components for identification of the sulfur and iron reducing and/or oxidizing bacterial species.

32. The kit of clause 31 wherein the components for identification of the sulfur and iron reducing and/or oxidizing bacterial species are selected from the group consisting of a purified nucleic acid comprising a sequence of SEQ ID NO: 1 to SEQ ID NO: 18, a heat stable DNA polymerase, a buffer, $MgCl_2$, $H_2O$, and instructions for use.

33. The kit of clause 30 further comprising instructions for the extraction and recovery of the sulfur and iron reducing and/or oxidizing bacterial species from the wall board.

34. A purified nucleic acid comprising a sequence of SEQ ID NO: 1 to SEQ ID NO: 18 or a sequence that hybridizes under highly stringent conditions to a sequence consisting of SEQ ID NO: 1 to SEQ ID NO: 18.

35. A purified nucleic acid comprising a complement of a sequence of SEQ ID NO: 1 to SEQ ID NO: 18 or a sequence that hybridizes under highly stringent conditions to a complement of a sequence consisting of SEQ ID NO: 1 to SEQ ID NO: 18.

DESCRIPTION OF THE ILLUSTRATIVE EMBODIMENTS

The present invention relates to methods and compositions for identifying or detecting iron and sulfur reducing and/or oxidizing bacteria in wall board and/or in patient body fluids and tissues. The identification and detection methods are based on amplification of bacterial DNA using a PCR-based method. The methods and compositions (e.g., primers and probes) for amplification of bacterial DNA are highly specific and sensitive and avoid co-amplification of or do not co-amplify non-specific human or animal nucleic acids or nucleic acids of other microorganisms.

In accordance with the invention, the phrase "wall board" means any type of wall board, for example, dry wall, manufactured in the United States of America or any foreign country (e.g., China). For example, the wall board can be normal dry wall, greenboard, paperless dry wall, and the like. Typically, the wall board (e.g., dry wall) comprises gypsum. The wall board can be presumed to be non-contaminated, or can be presumed to be contaminated.

In accordance with the invention the word "patient" means a human or an animal, such as a domestic animal (e.g., a dog or a cat). Accordingly, the methods and compositions disclosed herein can be used for both human clinical medicine and veterinary applications. Thus, the patient afflicted with a disease state related to a bacterial infection can be a human, or in the case of veterinary applications, can be a laboratory, agricultural, domestic or wild animal. The present invention can be applied to patients including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, chickens, and wild animals in captivity such as bears, pandas, lions, tigers, leopards, elephants, zebras, giraffes, gorillas, dolphins, and whales.

In various illustrative embodiments, patient body fluids and tissues that can be tested for the presence of bacterial DNA include, but are not limited to, urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, such as seminal fluid, lymph fluid, and whole blood, serum, or plasma. These samples can be prepared for testing as described herein. In various embodiments, tissue samples can include tissue biopsies of hospital patients or out-patients and autopsy specimens. As used herein, the term "tissue" includes, but is not limited to, biopsies, autopsy specimens, cell extracts, tissue sections, aspirates, tissue swabs, and fine needle aspirates.

The methods and compositions described herein can be used to detect or identify DNA of iron and sulfur reducing and/or oxidizing bacteria in microbes selected from the group consisting of *Acidothiobacillus ferroxidans* (i.e., *Thiobacillus ferroxidans*), *Acidothiobacillus thioxidans* (i.e., *Thiobacillus thioxidans*), *Leptospirillium ferroxidans*, *Acidothiobacillus caldus* (i.e., *Thiobacillus caldus*), *Desulfotomaculum ruminis*, and *Sulfobacillus thermosulfidooxidans*. In accordance with this invention, the phrase "reducing and/or oxidizing" means that the bacteria can reduce and oxidize both sulfur and iron, or can only reduce sulfur and iron, or can only oxidize sulfur and iron.

In one embodiment, multiple iron and sulfur reducing and/or oxidizing bacterial species can be identified in either wall board or patient tissues or body fluids using a PCR-based reaction in a highly specific and sensitive manner.

In one illustrative embodiment, a method is provided of identifying a specific iron and sulfur reducing and/or oxidizing bacterial species in wall board (e.g., dry wall) and in a patient tissue and/or body fluid. The method comprises the steps of extracting and recovering DNA of the bacterial species from the wall board and/or patient tissue and/or body fluid, amplifying the DNA, hybridizing a probe to the DNA to specifically identify the bacterial species, and specifically identifying the bacterial species.

In some embodiments, PCR-based methods can be used to amplify the bacterial DNA and to identify the bacterial DNA by hybridization of the probe to the bacterial DNA. PCR is described in U.S. Pat. Nos. 4,683,202 and 4,800,159, incorporated herein by reference, and methods for PCR are well-known in the art. Other methods include random amplified polymorphic DNA (RAPD) analysis and image analysis. An exemplary PCR-based method for use in the methods described herein is real-time PCR. Real-time PCR combines amplification and simultaneous probe hybridization to achieve sensitive and specific detection of infectious bacteria in real-time thereby providing instant detection of microorganisms. In this embodiment, the time to detect or identify the bacteria and to obtain an identification is greatly reduced. Real-time PCR is conducted according to methods well-known in the art. Exemplary probes and primers and their target DNAs that can be used in accordance with the invention are shown below. "Primer F" refers to a forward primer and "Primer R" refers to a reverse primer which are well-known terms in the art.

Target 1.- *Acidothiobacillus (Thiobacillus) caldus*
(Designed with strains N39-30-02, P5-10, MTH-04, DSM8584, DX-2, J-1, D-2, YN06, S-1, T-1, S-2, D-1)
Probe 1:
    (SEQ ID NO: 1)
5'-CGGGCTCAACCTGGGAATGGC Primer F1:
    (SEQ ID NO: 2)
5'-GTTACGTCTGCCGTGAAATCC Primer R1:
    (SEQ ID NO: 3)
5'-CTCCAGTCAGCCCGTTTCC Target 2.- *Sulfobacillus thermosulfidooxidans*
(Designed with strains HR-K17-45, DK-J16-45, DK-E8-45, N19-45-01, N19-50-01, G-2, YN22)
Probe 1:
    (SEQ ID NO: 4)
5'-CCCGGTAGTCCACGCCGTAAACG Primer F1:
    (SEQ ID NO: 5)
5'-GGGAGCGAACGGGATTAGAT Primer R1:
    (SEQ ID NO: 6)
5'-CCCGGGCGACACCTAGTAC Target 3.- *Leptospirillum ferrooxidans*
(Designed with strains JCM17, C2-6, C21, C2-3, C2-7, C2-2, C2-4)
Probe1:
    (SEQ ID NO: 7)
5'-CGGAGGCAATGCCGAGAGGC Primer F1:
    (SEQ ID NO: 8)
5'-GCAACAATGGCCGGTACAG Primer R1:
    (SEQ ID NO: 9)
5'-CGGTTTTCTCGGGTTTGCT Target 4.- *Acidothiobacillus (Thiobacillus) thioxidans*
(Designed with strains ATCC 19377)
Probe 1:
    (SEQ ID NO: 10)
5'-TGCTAATATCGCCTGCTGTTGACGTGA Primer F1:
    (SEQ ID NO: 11)
5'-TTCGTGGAGGACGAAAAGGT Primer R1:
    (SEQ ID NO: 12)
5' GCCGGTGCTTCTTCTTGGA Target 5. *Acidothiobacillus (Thiobacillus) ferrooxidans*
(Designed with strains ATCC23270T, ATCC33020, SS6, CC1, BRGM1, LMT1, LMT4, DSM9465, SS4, 64, ATCC19859, TF-49, B9, B20, B5, ML17-48A)
Probe 1:
    (SEQ ID NO: 13)
5'-Probe: CTAATACCGCATGAGCCCTG Primer F1:
    (SEQ NO: 14)
5'-TGGCGGACGGGTGAGTAATG Primer R1:
    (SEQ NO: 15)
5'-CCAGTGTGGCTGGTCGTC

```
Target 6: Desulfotomaculum ruminis
Probe 1:
                                                  (SEQ ID NO: 16)
5'-TGGGCGTAAAGGGCGCGTAGG Primer F1:
                                                  (SEQ ID NO: 17)
5'-CGAGCGTTGTCCGGAATTA Primer R1:
                                                  (SEQ ID NO: 18)
5'-CCCGCACTTTCACCTCTAACTT
```

In various embodiments, sample preparation (i.e., preparation of the target DNA) involves crushing wall board and/or tissue followed by rupturing the cells (e.g., cells of the bacteria found in wall board or tissue or body fluids) and isolating the bacterial DNA from the lysate. Techniques for rupturing cells and for isolation of DNA are well-known in the art. For example, cells may be ruptured by using a detergent or a solvent, such as phenol-chloroform. DNA may be separated from the lysate by physical methods including, but not limited to, centrifugation, pressure techniques, or by using a substance with affinity for DNA, such as, for example, silica beads. After sufficient washing, the isolated DNA may be suspended in either water or a buffer. In other embodiments, commercial kits are available, such as Quiagen™, Nuclisensm™, and Wizard™ (Promega), and Promegam™. Methods for isolating DNA are described in Sambrook et al., "Molecular Cloning: A Laboratory Manual", 3rd Edition, Cold Spring Harbor Laboratory Press, (2001), incorporated herein by reference.

In various embodiments described herein, the primers and probes used for amplification of the target DNA and for detection and identification of bacterial DNA are oligonucleotides from about ten to about one hundred, more typically from about ten to about thirty or about six to about twenty-five base pairs long, but any suitable sequence length can be used. In illustrative embodiments, the primers and probes may be double-stranded or single-stranded, but the primers and probes are typically single-stranded. The primers and probes described herein are capable of specific hybridization, under appropriate hybridization conditions (e.g., appropriate buffer, ionic strength, temperature, formamide, and MgCl$_2$ concentrations), to a region of the target DNA. The primers and probes described herein are designed based on having a melting temperature within a certain range, and substantial complementarily to the target DNA. Methods for the design of primers and probes are described in Sambrook et al., "Molecular Cloning: A Laboratory Manual", 3rd Edition, Cold Spring Harbor Laboratory Press, (2001), incorporated herein by reference.

The primers and probes described herein for use in PCR can be modified by substitution, deletion, truncation, and/or can be fused with other nucleic acid molecules wherein the resulting primers and probes hybridize specifically to the intended targets and are useful in the methods described herein for amplification of the target DNAs. Derivatives can also be made such as phosphorothioate, phosphotriester, phosphoramidate, and methylphosphonate derivatives, that specifically bind to single-stranded DNA or RNA (Goodchild, et al., Proc. Natl. Acad. Sci. 83:4143-4146 (1986)).

The invention encompasses isolated or substantially purified nucleic acids. An "isolated" or "purified" nucleic acid molecule is substantially free of other cellular material, or culture medium when produced by recombinant techniques, or substantially free of chemical precursors or other chemicals when chemically synthesized. In another embodiment, an "isolated" or "purified" nucleic acid is free of sequences that naturally flank the nucleic acid in the genomic DNA of the organism if derived from the genomic DNA. For example, in various embodiments, the isolated or purified nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Also within the scope of the invention are nucleic acids complementary to the probes and primers described herein, and those that hybridize to the nucleic acids described herein or those that hybridize to their complements under highly stringent conditions. In accordance with the invention "highly stringent conditions" means hybridization at 65° C. in 5×SSPE and 50% formamide, and washing at 65° C. in 0.5×SSPE. Conditions for low stringency and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

Also included are nucleic acid molecules having about 60%, about 70%, about 75%, about 80%, about 85%, about 90%, about 95%, 96%, 97%, and 98% homology to the probes and primers described herein. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid sequence of interest. Algorithms for database searching are typically based on the BLAST software (Altschul et al., 1990). In some embodiments, the percent identity can be determined along the full-length of the nucleic acid.

As used herein, the term "complementary" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary sequences can be DNA or RNA sequences. The complementary DNA or RNA sequences are referred to as a "complement."

Techniques for synthesizing the probes and primers described herein are well-known in the art and include chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Primers and probes can also be made commercially (e.g., CytoMol, Sunnyvale, Calif. or Integrated DNA Technologies, Skokie, Ill.). Techniques for purifying or isolating the probes and primers described herein are well-known in the art. Such techniques are described in Sambrook et al., "Molecular Cloning: A Laboratory Manual", 3rd Edition, Cold Spring Harbor Laboratory Press, (2001), incorporated herein by reference. The primers and probes described herein can be analyzed by techniques known in the art, such as restriction enzyme analysis or sequencing, to determine if the sequence of the primers and probes is correct.

In various embodiments of the methods and compositions described herein, the probes and primers can be labeled, such as with fluorescent compounds, radioactive isotopes, antigens, biotin-avidin, colorimetric compounds, or other labeling agents known to those of skill in the art, to allow detection and quantification of amplified DNA, such as by Real-Time PCR. In illustrative embodiments, the labels may include 6-carboxyfluorescein (FAM™), TET™ (tetrachloro-6-carboxyfluorescein), JOE™ (2,7, -dimethoxy-4,5-dichloro-6-carboxyfluorescein), VIC™, HEX (hexachloro-6-carboxyfluorescein), TAMRA™ (6-carboxy-N,N,N,N-tetramethylrhodamine), BHQ™, SYBR® Green, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, Oregon Green 488, Oregon Green 500, Oregon Green 514, Pacific Blue, REG, Rhodamine Green, Rhodamine Red, ROX, and/or Texas Red.

Specificity of the probes and primers described herein was demonstrated by testing hybridization of the probe and primers sets against 3 different bacterial organisms. There were no cross-over reactions or cross-over detection noted for any of the tested probe and primer sequences. Thus, the methods and compositions (e.g., primers and probes) for amplification of bacterial DNA are highly specific and avoid co-amplification of or do not co-amplify non-specific nucleic acids.

In one embodiment, a kit is provided. The kits are useful for identifying or detecting DNA of sulfur and iron reducing and/or oxidizing bacteria recovered from wall board (e.g., dry wall). In the embodiment where the kit is used to identify bacterial DNA, the kit can contain the probes and/or primers described herein, components to extract and isolate bacterial DNA, and components for DNA amplification, such as a heat stable DNA polymerase (e.g., Taq polymerase or Vent polymerase), buffers, $MgCl_2$, $H_2O$, and the like. The kit can also contain instructions for use.

In another embodiment, a kit comprising a purified nucleic acid with a sequence selected from the group consisting of SEQ ID NO: 1 to SEQ ID NO: 18 or a sequence that hybridizes under highly stringent conditions to a sequence consisting of SEQ ID NO: 1 to SEQ ID NO: 18 is provided.

In another embodiment, a kit comprising a purified nucleic acid with a sequence selected from the group consisting of SEQ ID NO: 1 to SEQ ID NO: 18 or a complement of a sequence selected from the group consisting of SEQ ID NO: 1 to SEQ ID NO: 18 is provided.

In another embodiment, a kit is provided that comprises components for the extraction and recovery of DNA of sulfur and iron reducing and/or oxidizing bacteria from wall board (e.g., dry wall). The kit can further comprise instructions for use.

Optionally, the kit described above can further comprise components for identification of the bacterial DNA as described above.

In one embodiment, the components for identification of the bacterial DNA for any of the kits described herein can also include beads dyed with a fluorochrome (e.g., Luminex®) and coupled to a probe for the bacterial DNA.

In one embodiment, the reagents for any of the kits described herein can remain in liquid form. In another embodiment, the reagents for any of the kits described herein can be lyophilized.

A purified nucleic acid is also provided comprising a sequence of SEQ ID NO: 1 to SEQ ID NO: 18 or a sequence that hybridizes under highly stringent conditions to a sequence consisting of SEQ ID NO: 1 to SEQ ID NO: 18.

A purified nucleic acid is also provided comprising a complement of a sequence of SEQ ID NO: 1 to SEQ ID NO: 18 or a sequence that hybridizes under highly stringent conditions to the complement of a sequence consisting of SEQ ID NO: 1 to SEQ ID NO: 18. In accordance with the invention "highly stringent conditions" means hybridization at 65° C. in 5×SSPE and 50% formamide, and washing at 65° C. in 0.5×SSPE.

In another embodiment, a method of treating wall board to eliminate a sulfur and iron reducing and/or oxidizing bacterial species in the wall board is provided, the method comprises the steps of treating the wall board with zeolite, and eliminating the sulfur and iron reducing and/or oxidizing bacterial species in the wall board. Illustratively, the zeolite can comprise elemental ions (e.g., $Ca^{+2}$, $Mg^{+2}$, etc.) that bind to the sulfur and iron reducing and/or oxidizing bacterial species and limit the growth of these organisms.

Commercial sources of zeolite include, but are not limited to, Bear River Zeolite Corporation, Thompson Falls, Mont. In one embodiment, the zeolite is used in solution as described in U.S. Pat. No. 7,384,622, incorporated herein by reference in its entirety.

In one illustrative embodiment, the zeolite solution is sprayed on wall board (e.g., dry wall) to eliminate a sulfur and iron reducing and/or oxidizing bacterial species in the wall board. In accordance with the invention, the terms "eliminate", "eliminating", and "eliminating" mean partially or completely inhibiting the growth of the sulfur and iron reducing and/or oxidizing bacterial species in the wall board, so that the sulfur and iron reducing and/or oxidizing bacterial species is not detectable in the wall board or is present in reduced amounts. In another embodiment, the concentration of zeolite in solution can vary from about 10% to about 60% weight/volume based on the type and amount of bacteria present in the wall board. In yet another embodiment, the zeolite solution described in the preceding paragraphs can be sprayed in air vents to eliminate a sulfur and iron reducing and/or oxidizing bacterial species in air vents and/or in room air.

The following examples provide illustrative methods for carrying out the practice of the present invention. As such, these examples are provided for illustrative purposes only and are not intended to be limiting.

Example 1

Samples and Sample Preparation

Analysis on Wallboard (Dry Wall):

Pieces of gypsum wallboard were cut into 1.0"×1.0"×0.25" pieces. The bacteria was harvested from the wall board by mastication (blending) the dry wall in 12 ml. of sterile distilled water. Another method is to take the same amount of dry wall and crush it in a sterile mortar and pestle. The powder is removed and stored in a sterile tube. 0.3-0.4 gm of crushed dry wall is transferred to a tube containing 0.3 gm of sterile glass beads and 1.0 ml of sterile distilled water in a 2.0 ml tube. The masticated wall board may also be used by removing 1.5 ml of solution and placing in a 2.0 ml tube containing 0.3 sterile glass beads. Both samples can then be subjected to the extraction methods listed below.

The following methods can be applied to tissue samples, body fluid samples, or drywall.

Extraction Methods:

Bead Beater Tube Preparation:

1. 0.3 g±0.01 g of silica bead beating glass (Sigma-Aldrich Cat. no G1277) was added to 2 ml screw cap tube avoiding glass beads in the cap or around the rim.

2. The tubes containing the beads were sterilized in an autoclave on the dry cycle for 10 minutes.
3. The tubes were removed from the autoclave.

Solution Preparation:

4. Buffers ATL (from DNAeasy® Tissue Kit, Cat. no. 69506 (Quiagen, Stanford Valencia, Calif.)) and AL (from DNAeasy® Tissue Kit, Cat. no. 69506) may form precipitates upon storage. If a precipitate formed in either buffer, the buffer was incubated at 55° C. until the precipitate fully dissolved.
5. Buffers AW1 and AW2 (from DNAeasy® Tissue Kit, Cat. no. 69506) were supplied as concentrates. Before using for the first time, the appropriate amounts of ethanol (96-100%) were added to Buffers AW1 and AW2 as indicated on the bottles.
6. A 55° C. heat block and a 70° C. heat block were prepared for use in the assay.

Preparation of the Wall Board or Tissue:

7. If frozen material was used, it was equilibrated to room temperature.
8. 0.3 gm-0.4 gm of powdered wall board which is obtained from taking a 1 inch square of dry wall and then crushed in a sterile mortar and pestle. The dry wall may also be blended with 12 ml of sterile saline for 1 minute. 1 ml of the solution may also be used in place of the powdered solution. All specimens are placed in a 2.0 ml screw cap tube with 0.3 gm of sterile beads.
9. 180.0 μl of ATL Buffer and 20.0 μl of Proteinase K was added to each sample making sure that the lysate was not gelatinous.
10. 10.0 μl of the Geo Spore reference DNA was added to each sample as an internal control. (See Assay Specific Procedure for information regarding internal and external controls)
11. All samples were bead beated on the Bead Beater for 1 minute at the speed of 45.
12. Samples were incubated at 55° C. on a pre-warmed heat block for 1 hour.

Extraction of Nucleic Acid:

15. The samples were removed from the heat block and vortexed 15 seconds.
16. 200 μl of Buffer AL was added and incubated at 70° C. for 10 minutes.
17. The tubes were removed from the 70° C. heat block and add 200 μl of ethanol
18. 200 μl of ethanol was added to each tube and vortexed.
19. The mixture is centrifuged for 20 sec at 8000 rpm and the supernatant is removed, making sure not to pipette the silica beads, into the corresponding DNeasy® Mini Spin Column 2 ml collection tube combo for that sample.
20. The columns were centrifuged in a microcentrifuge at 8000 RPM for 1 minute. The collection tube containing the flow through was discarded.
21. Each spin column was placed in a new 2.0 ml collection tube.
22. 500.0 μl of Buffer AW1 was added to each column and centrifuged at 8000 RPM for 1 minute. The collection tube containing the flow through was discarded.
23. Each spin column was placed in a new 2.0 ml collection tube.
24. 500 μl of Buffer AW2 was added to each column and centrifuged at 13,000 RPM for 5 minute.
25. The spin columns were removed carefully from the collection tubes so as not to splash nozzles. The collection tube containing the flow through was discarded.
26. The spin columns were placed in their corresponding 1.5 ml elution tube.
27. 100 μl of Buffer AE (from DNAeasy® Tissue Kit, Cat. no. 69506) was placed into each spin column and incubated for 3 minutes at room temperature.
28. The spin columns were centrifuged at 8000 RPM for 1 minute. The spin columns were discarded and capped and the extracted nucleic acid samples were stored at −20° C.

Real-Time PCR:

Preparation and Reaction Setup

11. Dilution of Probe Stocks
    a. Resuspend the lyophilized probes in PCR grade water to a final concentration of 100 μM.
       (Example: If the synthesis yields 15.03 nMoles, add 150.3 of PCR grade water to achieve 100 μM concentration)
2. Dilution of Primer Stocks
    a. Resuspend the lyophilized primers in PCR grade water to a final concentration of 100 μM.
       (Example: If the synthesis yields 38.6 nMoles, add 386 μl of PCR grade water to achieve 100 μM concentration)
3. Preparation of Primer/Probe Working Stock
    a. See Appendix A for the working Stock setup for each target.
4. Reaction Setup
    a. The reaction setup for one reaction is shown below. In some cases the addition of $MgCl_2$ or varying concentrations of primer/probe mix is required for PCR. (See Appendix A)

| | |
|---|---|
| DNA | 5.0 μl |
| Primer/Probe Working Stock | 3.5 μl (Final Concentration see appendix A) |
| OmniMix Beads | 0.5 μl Beads (no volume contribution) |
| PCR Grade Water | 16.5 μl |
| Total | 25.0 μl |

(Note that during reaction setup a master mix will be prepared for multiple reactions using the Smart Cycler PCR Worksheet (20.4007F). See following sections.)

5. Smart Cycler Cycling Parameters (Omni Fungal I)
    a. Omni bacterial I is the primary program used for the bacterial (microbial) real time assays and the run parameters for this program are outlined below, and are described in U.S. Appl. Publ. No. 2008/0014582, incorporated herein by reference. Cases may occur where changes to this program may be necessary for a specific target or specimen type. See SmartCycler Operation (20.2008S) for further instruction on programming and run optimization utilizing the Smart Cycler software.
       Step 1 (1 Cycle)
          Hot Start: 95° C. for 120 seconds
       Step 2 (45 cycles)
          Denature: 95° C. for 5 seconds
          Anneal: 60° C. for 45 seconds
See Example PCR Worksheet below: (Note: sheet has been truncated to show 3 target sets.)

II. Master Mix Setup

| Reagent | Lot # | Volume (μL) | Reaction No. | Total Amount | Target |
|---|---|---|---|---|---|
| Set 1 | | | | | |
| 1 H$_2$O | 4532 | 16.5 | 4 | 66.0 | Thiobacillus |
| 2 P/P Working Stock | 040505 | 3.5 | 4 | 14.0 | ferrooxidans |
| 3 Omni Mix (Bead) | 2456 | 0.5 | 4 | 2.0 | |
| 4 MgCl$_2$ | NA | 0.0 | 0 | 0.0 | |
| Set 2 | | | | | |
| 1 H$_2$O | 4532 | 16.5 | 4 | 66.0 | Thiobacillus |
| 2 P/P Working Stock | 020705 | 3.5 | 4 | 14.0 | caldus |
| 3 Omni Mix (Bead) | 2456 | 0.5 | 4 | 2.0 | |
| 4 MgCl$_2$ | NA | 0.0 | 0 | 0.0 | |
| Set 3 | | | | | |
| 1 H$_2$O | 4532 | 16.5 | 4 | 66.0 | (6) Geo |
| 2 P/P Working Stock | 020705 | 3.5 | 4 | 14.0 | |
| 3 Omni Mix (Bead) | 2456 | 0.5 | 4 | 2.0 | |
| 4 MgCl$_2$ | NA | 0.0 | 0 | 0.0 | |

*Add MgCl$_2$ as needed per target subtract volume used from water added to maintain a 20 μl reaction.
Add 20 μl of Master Mix to each tube and then add 5.0 μl of template for a total volume of 25.0 μL.

APPENDIX A—TARGET WORKING STOCK RECIPES

A. Rehydration of Lyophilized Stocks.

All lyophilized stocks were rehydrated to 100 μM concentration. Master Mix Stocks were made for each assay by using the following formulation for 700 μL of Master Mix Stock:

| | |
|---|---|
| Primer 1 | 15.0 μL |
| Primer 2 | 15.0 μL |
| Probe | 10.0 μL |
| Water | 660 μL |
| Total | 700 μL |

B. Master Mix Preparation and testing:
1. All steps were performed under sterile conditions.
2. After the water and beads had been pipetted into to the individual tubes, the tubes were mixed until the beads (Cat no. Omni 1-100N-050; Cepheid, Sunnyvale, Calif.) were completely dissolved.
3. After the beads were dissolved, the appropriate primer/probe working stock was pipetted into each master mix tube as described in the PCR worksheet.
4. The solutions were mixed completely and the working stocks returned to the −20° C. freezer.
5. Controls—
   a. Internal Control—Every clinical sample processed was inoculated with spores from the internal control target Geometrica to show that a negative target result is a true negative result and not related to the extraction of the sample. The samples were processed through the extraction protocol and amplified and detected utilizing primer and probes specific for Geometrica.
   b. Positive Control—A positive control for each target of interest (Primer/Probe sets) was processed along with each clinical sample in each real-time PCR run. This positive control can be extracted from wall board or tissue or body fluid but must be lot checked prior to use. The positive control shows that the primer/probe set for each target is not being inhibited and shows that a negative result is a true negative.
   c. Negative Control—A negative control for each target of interest (Primer/Probe sets) was processed along with each clinical sample in each real-time PCR run. This negative control can be extracted from dry wall, tissue, body fluids, or water but must be lot checked prior to use. The negative control shows that the primer/probe set, water and extraction reagents for each target is not contaminated with the target and shows that a positive result is a true positive.

Addition of Target Nucleic acid:
1. 5.0 μl of the negative control, positive control and patient samples was pipetted into the appropriate reaction tubes.
2. The reaction tubes were centrifuged using the Smart Cycler® II modified centrifuge.
3. The tubes were returned to the cooling block and stored at 4° C. or the Smart Cycler Setup and Run was conducted.

Smart Cycler Setup and Run:
1. The Omni Fungal I protocol or the appropriate protocol was selected for this real-time run.
2. For information regarding the operation of the Smart Cycler see SmartCycler Operation (20.2008S) (Smart Cycler® II Instrument; Cepheid, Sunnyvale, Calif.).

Data Analysis:
1. After the run is completed the results were analyzed by reviewing each site in the results table. If a specific sample tested was registered as positive by the software there was a positive in the results column for that sample. There was also a crossing point registered in the Ct column for that sample.
2. After reviewing the Results Table, the curves were reviewed for each sample by selecting the "FAM" or "Log FAM" of the "Views" menu.
3. With the graph selected, all samples that created a curve were present on the screen. Each sample was reviewed independently by clicking on the Site ID associated with the sample of interest located just to the right of the graph.
4. A sample was analyzed as positive by the software if the curve broke the baseline of 30 (default set in section above) before the end of the 45 cycles and negative if it did not break the baseline of 30 before the end of the 45 cycles.
5. Each sample was reviewed and then highlighted so that all sample curves were present on the graph.

Results Interpretation:
1. Positive Result: A positive result is defined as any amplification observed crossing a baseline fluorescence of ≥20 between cycles 1 and 40 of the real-time PCR run.
2. Negative Result: A negative result is defined as no amplification observed crossing a baseline fluorescence of ≥20 between cycles 1 and 40 of the PCR run.
3. Equivocal Result: An equivocal result is defined as no amplification observed crossing a baseline fluorescence of ≥20 between cycles 1 and 40, a control out of range or questions regarding sample integrity.

4. Positive Control: A control that is positive for the target being tested and shows that the assay will show a positive in the presence of target spores and that there is not PCR inhibition.
5. Negative Control: A control that is negative for the target being tested and shows that the reagents or the sample were not contaminated with the target prior to the testing of the sample.
6. Internal Control: A control used to show that the extraction process is working fine for the purification of nucleic acid from the clinical specimen and that a negative result is truly negative and not due to an issue associated with the extraction. (Note: the internal control must be positive for any sample to be reported as negative for a target.)

See Table Below:

|  | Crossing Point | Positive Control | Negative Control | Internal Control |
|---|---|---|---|---|
| Reportable Result |  |  |  |  |
| Positive Result | ≥40 | (+) | (−) | (+) |
| Positive Result | ≥40 | (−) | (−) | (+) |
| Positive Result | ≥40 | (+) | (−) | (−) |
| Positive Result | ≥40 | (−) | (−) | (−) |
| Negative Result | (−) | (+) | (−) | (+) |
| Negative Result | (−) | (+) | (+) | (+) |
| Negative Result | (−) | (−) | (+) | (+) |
| Un-reportable Result |  |  |  |  |
| Positive Result | ≥40 | (+) | (+) | (+) |
| Positive Result | ≥40 | (−) | (+) | (+) |
| Positive Result | ≥40 | (+) | (+) | (−) |
| Positive Result | ≥40 | (−) | (+) | (−) |
| Negative Result | (−) | (−) | (−) | (+) |
| Negative Result | (−) | (+) | (−) | (−) |
| Negative Result | (−) | (+) | (+) | (−) |
| Equivocal Result |  |  |  |  |
| Case by Case | Case by Case | Case by Case | Case by Case | Case by Case |

In other illustrative embodiments, results can be determined based on a cycle range between cycles 1 and 45 of the PCR run or other useful ranges can be used.

C. Standard Curves:

Assays for *Thiobacillus caldus, S. thermosulfidooxidans*, and *A. ferroxidans* were optimized utilizing target DNA in 10-fold serial dilutions formulating a curve. Data was collected and evaluated and the assays were determined to be optimized to the specification of RealTime Laboratories. (Runs 092809.1 and 92809.2).

D. Testing of Spiked Wallboard:

Assays for *T. caldus, S. thermosulfidooxidans*, and *A. ferroxidans* were further tested by spiking known organisms into wallboard that was not contaminated with any organisms. This wallboard was tested for each organism as well as a positive control and a negative wallboard sample. In all cases, the organism was detected. See runs 092809.3.

E. Testing of Wallboard Unknowns:

Assays for *T. caldus, S. thermosulfidoxoidans, A. ferroxidans, L. ferroxidans*, and *A. thioxidans* using primers and probes were run against 6 unknown wallboard samples. *A. ferroxidans* produced positive results in all six samples and a possible positive with *T. caldus*. See runs 092909.1, 092909.2, 092909.3.

F. Testing of Concentrated Wallboard unknowns.

Assays for *T. caldus* and *A. ferroxidans* were run with concentrated version of samples 3,10, and 11 were conducted to obtain stronger results. Such results were obtained. See run 092909.4 and 093009.1.

Example 2

Zeolite Preparation

Illustratively, zeolite will be prepared as described in U.S. Pat. No. 7,384,622, incorporated herein by reference. The zeolite will be emulsified using a fine mesh of about 4 to about 10 microns (Bear River Zeolite Corporation, Thompson Falls, Mont.) in a solution comprising TEOS (Tetraethyl orthosilicate ($Si(OC_2H_5)_4$)), TBAOH (Tetrabutylammonium hydroxide (($C_4H_9)_4NOH$)), water, and ethanol and the solution will be subjected to hydrothermal crystallization treatment to produce MEL-type zeolite nanocrystals as described in the U.S. Pat. No. 7,384,622. In one illustrative embodiment, the zeolite solution will be sprayed on wall board (e.g., dry wall) to eliminate a sulfur and iron reducing and/or oxidizing bacterial species in the wall board. The concentration of the zeolite in solution will vary from about 10% to about 60% weight/volume based on the type and amount of bacteria present in the wall board. The zeolite solution will also be sprayed in air vents to eliminate a sulfur and iron reducing and/or oxidizing bacterial species in air vents and/or in room air.

Example 3

Detection of *Sulfobacillus thermosulfidooxidans* and *Actinobacillus thioxidans* in Drywall A. Preparation of Samples:

The following materials can be used in the preparation of samples: Wizard SV Genomic DNA Purification System (Promega Corporation), Lysozyme (Sigma Aldrich), Glass Beads, Acid Washed (Sigma Aldrich), Proteinase K (Amresco), EDTA (0.5M), 10×PBS at pH 7.4, 1.7 mL micro tubes, and 15 mL conical tubes. Prior to sample preparation, 1.7 mL micro tubes can be prepared with 0.15 g of acid washed glass beads for each sample. The lysozyme mixture can be prepared by adding 80 µL of 50 mg/mL lysozyme in 320 µL of 0.5M EDTA in a tube for use per sample. The nuclei lysis solution can be prepared by combining 473 µL of Nuclei Lysis, 7.0 µL of Rnase A, and 20.0 µL of Proteinase K Solution in a tube for use per sample.

Procedure:

1. Measure 1.0 grams of drywall and place in a 15 mL conical tube. Add 1.0 mL of 10×PBS pH 7.4.
2. Vortex to disperse the drywall in the PBS. Immediately pipette 1.5 mL of drywall solution into a 1.7 mL tube containing 0.15 g pf acid washed glass beads.
3. Spin 1.7 mL tube in a microcentrifuge for 5 minutes at 13000 RCF to pellet the drywall.
4. Remove as much of the supernatant as possible and discard.
5. To sample tube containing pellet add 10.0 µL of GEO spores.

6. To sample tube containing pellet add 400 µL of lysozyme (10 mg/mL) mixture making sure solution covers the pellet.
7. Vortex for approximately 1.0 minute and incubate at 37° C. for 30 minutes.
8. After the incubation, add 500 µL of Nuclei Lysis Solution to the sample tube and vortex briefly.
9. Incubate sample tube at 55° C. for 30 minutes then vortex the sample tube briefly.
10. To deactivate the enzymes, incubate sample tube at 80° C. for 10 minutes.
11. Remove sample from the 80° C. heat block and vortex briefly and spin down the sample utilizing a quick spin. If necessary to improve recovery, multiple aliquots from the same drywall sample can be processed through the above steps and combined into one minicolumn assembly in the following steps below.
12. Pipette all supernatant from the sample tube and place in a minicolumn assembly making sure not to displace any of the pelleted material at the bottom of tube.
13. Place column assembly containing the supernatant in a 1.7 mL microcentrifuge and spin at 13,000 RCF for 3 minutes.
14. After spin, remove assembly and discard the waste in the collection tube.
15. Reassemble the column and collection tube and pipette 550 µL of SV Wash solution in the column. Place assembly in the centrifuge and spin at 13,000 RCF for 1 minute.
16. Repeat the above step two more time for a total of three wash steps.
17. After the final wash step, dry the column by placing the column assembly into the microcentrifuge and centrifuge at 16,000 RCF for 4.5 minutes.
18. After the drying spin, place column in a clean 1.7 mL tube.
19. Elute DNA by pipetting 100.0 µL of 55° C. warmed nuclease free water into the column. Place the 1.7 mL tube containing the column into the microcentrifuge and spin at 13,000 RCF for 1 minute.
20. The DNA is now ready for processing utilizing realtime PCR.

B. PCR Assay:

The following materials can be used in the PCR assay: TaqMan Fast Universal PCR Master Mix (2×) (Applied Biosystems), MicroAmp Fast Optical 96-Well Reaction Plates (Applied Biosystems), Optical Adhesive Covers (Applied Biosystems), molecular grade water, and assay-dependent primers and probes.

Procedure:

Reaction Setup—

| Assay 1 | | RXN # | 0 | Plus (10%) | 0.0 |
|---|---|---|---|---|---|
| 20.0 µL Reaction with 19.0 µL of Master Mix and 1.0 µL of DNA | | | | | |
| | Man/Lot | Stock Conc. | Work Conc. | Per/RXN | Master mix |
| 2x mm | | 2X | 1X | 10.0 | 0.0 |
| Primer 1 | | 10 µM | 0.5 µM | 1.0 | 0.0 |
| Primer 2 | | 10 µM | 0.5 µM | 1.0 | 0.0 |
| Probe 1 | | 2.5 µM | 0.1 µM | 0.8 | 0.0 |
| Water | | na | na | 6.2 | 0.0 |

Cycling Profile:

| Step No. | Temperature | Time |
|---|---|---|
| Step 1 | 95.0° C. | 0.20 |
| Step 2 | 95.0° C. | 0.03 |
| Step 3 | 60.0° C. | 0.30 |

Repeat Steps 2 and 3 for 45 cycles with signal recorded at the end of cycle 3.

C. Results:

*Sulfobacillus thermosulfidooxidans*

| | | *Sulfobacillus thermosulfidooxidans* | | Assays | |
|---|---|---|---|---|---|
| ID | Well | Name/ID | Ct | Ct Internal Control | Results |
| 1 | A1 | EN0410009 | Undetermined | na | Not Detected |
| 2 | A2 | EN0410008 | Undetermined | na | Not Detected |
| 3 | A3 | EN0410007 | Undetermined | na | Not Detected |
| 4 | A4 | EN0410006 | Undetermined | na | Not Detected |
| 5 | A5 | EN0310005 | Undetermined | na | Not Detected |
| 6 | A6 | EN9310009 | Undetermined | na | Not Detected |
| 7 | A7 | EN0310007 | Undetermined | na | Not Detected |
| 8 | A8 | EN0310006 | Undetermined | na | Not Detected |
| 9 | A9 | EN0310003 | Undetermined | na | Not Detected |
| 10 | A10 | EN0310004 | Undetermined | na | Not Detected |
| 11 | A11 | EN0510024 | 34.2409 | na | Positive |
| 12 | A12 | EN0510025 | 35.1339 | na | Positive |
| 13 | B1 | EN0510027 | 34.2176 | na | Positive |
| 14 | B2 | EN0510028 | 39.0069 | na | Positive |
| 15 | B3 | EN0510030 | 35.5586 | na | Positive |
| 16 | B4 | EN0510031 | Undetermined | na | Some Amplification |
| Control | B5 | Pos Control | 39.3907 | na | Positive |
| Media Control | B6 | EN0510033 | Undetermined | na | Not Detected |
| Control | B7 | NTC | Undetermined | na | Not Detected |

*Actinobacillus thioxidans*

| | | *Actinobacillus thioxidans* | | Assays | |
|---|---|---|---|---|---|
| ID | Well | Name/ID | Ct | Ct Internal Control | Results |
| 1 | D1 | EN0410009 | Undetermined | na | Not Detected |
| 2 | D2 | EN0410008 | Undetermined | na | Not Detected |
| 3 | D3 | EN0410007 | Undetermined | na | Not Detected |
| 4 | D4 | EN0410006 | Undetermined | na | Not Detected |
| 5 | D5 | EN0310005 | Undetermined | na | Not Detected |
| 6 | D6 | EN9310009 | Undetermined | na | Not Detected |
| 7 | D7 | EN0310007 | Undetermined | na | Not Detected |
| 8 | D8 | EN0310006 | Undetermined | na | Not Detected |
| 9 | D9 | EN0310003 | Undetermined | na | Not Detected |
| 10 | D10 | EN0310004 | Undetermined | na | Not Detected |
| 11 | D11 | EN0510024 | 36.6029 | na | Positive |
| 12 | D12 | EN0510025 | 38.5925 | na | Positive |
| 13 | E1 | EN0510027 | Undetermined | na | Not Detected |
| 14 | E2 | EN0510028 | Undetermined | na | Not Detected |
| 15 | E3 | EN0510030 | Undetermined | na | Not Detected |
| 16 | E4 | EN0510031 | Undetermined | na | Not Detected |
| Control | E5 | Pos Control | 18.3747 | na | Positive |
| Media Control | E6 | EN0510033 | 38.045 | na | Positive |
| Control | E7 | NTC | Undetermined | na | Not Detected |

Thiobacillus ferrooxidans

| | | | Assays | | |
|---|---|---|---|---|---|
| | | *Thiobacillus ferrooxidans* | | Ct Internal | |
| ID | Well | Name/ID | Ct | Control | Results |
| 1 | A1 | EN0410002 | Undetermined | na | Not Detected |
| 2 | A2 | EN0410003 | Undetermined | na | Not Detected |
| 3 | A3 | EN0410005 | Undetermined | na | Not Detected |
| 4 | A4 | EN0310008 | Undetermined | na | Not Detected |
| 5 | A5 | EN0410004 | Undetermined | na | Not Detected |
| 6 | A6 | EN0410009 | Undetermined | na | Not Detected |
| 7 | A7 | EN0410008 | Undetermined | na | Not Detected |
| 8 | A8 | EN0410007 | Undetermined | na | Not Detected |
| 9 | A9 | EN0410006 | Undetermined | na | Not Detected |
| 10 | A10 | EN0310002 | Undetermined | na | Not Detected |
| 11 | A11 | EN0310005 | Undetermined | na | Not Detected |
| 12 | A12 | EN0310009 | Undetermined | na | Not Detected |
| 13 | B1 | EN0310007 | Undetermined | na | Not Detected |
| 14 | B2 | EN0310006 | Undetermined | na | Not Detected |
| 15 | B3 | EN0310001 | Undetermined | na | Not Detected |
| 16 | B4 | EN0310003 | Undetermined | na | Not Detected |
| 17 | B5 | EN0310004 | Undetermined | na | Not Detected |
| 18 | B6 | thioxidans | Undetermined | na | Not Detected |
| 19 | B7 | ferroxidans | Undetermined | na | Not Detected |
| 20 | B8 | EN0510023 | Undetermined | na | Not Detected |
| 21 | B9 | EN0510024 | Undetermined | na | Not Detected |
| 22 | B10 | EN0510025 | Undetermined | na | Not Detected |
| 23 | B11 | EN0510026 | Undetermined | na | Not Detected |
| 24 | B12 | EN0510027 | Undetermined | na | Not Detected |
| 25 | C1 | EN0510028 | Undetermined | na | Not Detected |
| 26 | C2 | EN0510029 | Undetermined | na | Not Detected |
| 27 | C3 | ENO510030 | Undetermined | na | Not Detected |
| 28 | C4 | EN0510031 | Undetermined | na | Not Detected |
| 29 | C5 | EN0510033 | Undetermined | na | Not Detected |
| 30 | C6 | EN0510032 | Undetermined | na | Not Detected |
| Control | C7 | Pos Control | 31.9468 | na | Positive |
| Control | C8 | NTC | Undetermined | na | Not Detected |

Thiobacillus caldus

| | | | | Assays | | |
|---|---|---|---|---|---|---|
| | | *Thiobacillus caldus* | | | Ct Internal | |
| ID | Well | Name/ID | Sex | Ct | Control | Results |
| 1 | A1 | EN0510057 | ? | Undetermined | na | Not Detected |
| 2 | A2 | EN0510059 | ? | Undetermined | na | Not Detected |
| 3 | A3 | EN0510061 | ? | Undetermined | na | Not Detected |
| 4 | A4 | EN0510063 | ? | Undetermined | na | Not Detected |
| Control | A5 | Pos | ? | 23.7406 | na | Positive |
| Control | A6 | NTC | ? | Undetermined | na | Not Detected |

Sulfobacillus thermosulfidooxidans

| | | | | Assays | | |
|---|---|---|---|---|---|---|
| | | *Sulfobacillus thermosulfidooxidans* | | | Ct Internal | |
| ID | Well | Name/ID | Sex | Ct | Control | Results |
| 1 | A7 | EN0510057 | ? | Undetermined | na | Not Detected |
| 2 | A8 | EN0510059 | ? | Undetermined | na | Not Detected |
| 3 | A9 | EN0510061 | ? | Undetermined | na | Not Detected |
| 4 | A10 | EN0510063 | ? | Undetermined | na | Not Detected |
| Control | A11 | Pos | ? | 38.5395 | na | Positive |
| Control | A12 | NTC | ? | Undetermined | na | Not Detected |

Actinobacillus thioxidans

| | | | | Assays | | |
|---|---|---|---|---|---|---|
| | | *Actinobacillus thioxidans* | | | Ct Internal | |
| ID | Well | Name/ID | Sex | Ct | Control | Results |
| 1 | B1 | EN0510057 | ? | Undetermined | na | Not Detected |
| 2 | B2 | EN0510059 | ? | Undetermined | na | Not Detected |
| 3 | B3 | EN0510061 | ? | Undetermined | na | Not Detected |
| 4 | B4 | EN0510063 | ? | Undetermined | na | Not Detected |
| Control | B5 | Pos | ? | 17.3068 | na | Positive |
| Control | B6 | NTC | ? | Undetermined | na | Not Detected |

Thiobacillus ferrooxidans

| | | | | Assays | | |
|---|---|---|---|---|---|---|
| | | *Thiobacillus ferrooxidans* | | | Ct Internal | |
| ID | Well | Name/ID | Sex | Ct | Control | Results |
| 1 | B7 | EN0510057 | ? | Undetermined | na | Not Detected |
| 2 | B8 | EN0510059 | ? | Undetermined | na | Not Detected |
| 3 | B9 | EN0510061 | ? | Undetermined | na | Not Detected |
| 4 | B10 | EN0510063 | ? | Undetermined | na | Not Detected |
| Control | B11 | Pos | ? | 21.1885 | na | Positive |
| Control | B12 | NTC | ? | Undetermined | na | Not Detected |

Leptospirdlum ferrooxidans

| | | | | Assays | | |
|---|---|---|---|---|---|---|
| | | *Leptospirillum ferrooxidans* | | | Ct Internal | |
| ID | Well | Name/ID | Sex | Ct | Control | Results |
| 1 | C1 | EN0510057 | ? | Undetermined | na | Not Detected |

| | | Assays | | | | |
|---|---|---|---|---|---|---|
| | | *Leptospirillum ferrooxidans* | | | Ct Internal | |
| ID | Well | Name/ID | Sex | Ct | Control | Results |
| 2 | C2 | EN0510059 | ? | Undetermined | na | Not Detected |
| 3 | C3 | EN0510061 | ? | Undetermined | na | Not Detected |
| 4 | C4 | EN0510063 | ? | Undetermined | na | Not Detected |
| Control | C5 | NTC | ? | Undetermined | na | Not Detected |

What is claimed is:

1. A method of identifying a specific iron and sulfur reducing and/or oxidizing bacterial species in wall board, the method comprising the steps of:
   extracting and recovering DNA of the bacterial species from the wall board, amplifying the DNA;
   hybridizing a probe to the DNA to specifically identify the bacterial species; and
   specifically identifying the bacterial species, wherein the probe, a forward primer, and a reverse primer are used during the amplification step, and wherein the probe consists of a sequence selected from the group consisting of SEQ ID NO: 1, SEQ ID NO: 7, and SEQ ID NO: 16.

2. The method of claim 1 wherein the amplifying step is performed with a primer that hybridizes to the DNA.

3. The method of claim 1 wherein the wall board is dry wall.

4. The method of claim 1 wherein the DNA is amplified using PCR.

5. The method of claim 4 wherein the PCR is real-time PCR.

6. The method of claim 1 wherein the probe is fluorescently labeled.

7. The method of claim 2 wherein the primer is fluorescently labeled.

8. The method of claim 1 wherein the bacterial species is selected from the group consisting of *Leptospirillium ferroxidans, Thiobacillus caldus*, and *Desulfotomaculum ruminis*.

9. The method of claim 2 wherein the forward primer comprises the sequence of SEQ ID NO: 2 and the reverse primer comprises the sequence of SEQ ID NO: 3.

10. The method of claim 2 wherein the forward primer comprises the sequence of SEQ ID NO: 8 and the reverse primer comprises the sequence of SEQ ID NO: 9.

11. The method of claim 2 wherein the forward primer comprises the sequence of SEQ ID NO: 17 and the reverse primer comprises the sequence of SEQ ID NO: 18.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
cgggctcaac ctgggaatgg c                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gttacgtctg ccgtgaaatc c                                               21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctccagtcag cccgtttcc                                                  19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cccggtagtc cacgccgtaa acg                                             23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 5
gggagcgaac gggattagat                                              20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccgggcgac acctagtac                                               19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cggaggcaat gccgagaggc                                              20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcaacaatgg ccggtacag                                               19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggttttctc gggtttgct                                               19

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tgctaatatc gcctgctgtt gacgtga                                      27

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttcgtggagg acgaaaaggt                                            20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccggtgctt cttcttgga                                             19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ctaataccgc atgagccctg                                            20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggcggacgg gtgagtaatg                                            20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccagtgtggc tggtcgtc                                              18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tgggcgtaaa gggcgcgtag g                                          21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
cgagcgttgt ccggaatta                                                    19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cccgcacttt cacctctaac tt                                                22
```